(12) United States Patent  
O'Connell

(10) Patent No.: US 8,123,733 B2  
(45) Date of Patent: Feb. 28, 2012

(54) ABSORBENT ARTICLE WITH INTERMITTENT SIDE SEAMS

(75) Inventor: Susan O'Connell, State College, PA (US)

(73) Assignee: First Quality Baby Products, LLC, Great Neck, NY (US)

( * ) Notice: Subject to any disclaimer, the term of this patent is extended or adjusted under 35 U.S.C. 154(b) by 181 days.

(21) Appl. No.: 12/362,360

(22) Filed: Jan. 29, 2009

(65) Prior Publication Data

US 2010/0191213 A1 Jul. 29, 2010

(51) Int. Cl.
*A61F 13/15* (2006.01)
(52) U.S. Cl. ............... 604/389; 604/396; 604/385.03; 604/391; 604/390; 604/387
(58) Field of Classification Search .............. 604/389, 604/396, 385.03, 391, 390, 387
See application file for complete search history.

(56) References Cited

U.S. PATENT DOCUMENTS 3,039,466 A 6/1962 Wilson
(Continued)

FOREIGN PATENT DOCUMENTS

EP 0217032 B1 10/1992
(Continued)

OTHER PUBLICATIONS

International Search Report of PCT/US2010/022410 dated Mar. 23, 2010.
(Continued)

*Primary Examiner* — Jacqueline F. Stephens
(74) *Attorney, Agent, or Firm* — Amster, Rothstein & Ebenstein LLP

(57) ABSTRACT

An absorbent article has an inside surface that faces a wearer's body when the absorbent article is worn, and an outside surface opposite the inside surface. The absorbent article includes a liquid pervious topsheet and a backsheet, at least a portion of the backsheet being liquid impervious. A front waist portion includes a first side front panel and a second side front panel. A back waist portion includes a first side back panel and a second side back panel. A crotch portion longitudinally extends between the front waist portion and the back waist portion. An absorbent assembly is disposed between the topsheet and the backsheet. A first fastening component is disposed at the first side front panel and a second fastening component is disposed at the second side front panel for respective attachment to the first side back panel and the second side back panel to fasten the absorbent article around the waist of the wearer. The first and second fastening components each have at least one active fastening portion and at least one non-active fastening portion.

12 Claims, 6 Drawing Sheets

U.S. PATENT DOCUMENTS

| | | | |
|---|---|---|---|
| 3,842,837 A | 10/1974 | Sward | |
| 4,122,552 A | 10/1978 | Tedford | |
| 4,145,763 A | 3/1979 | Abrams et al. | |
| 4,205,679 A | 6/1980 | Repke et al. | |
| 4,244,368 A | 1/1981 | Caradonna | |
| 4,253,461 A | 3/1981 | Strickland et al. | |
| 4,293,456 A | 10/1981 | Reischl | |
| 4,402,690 A | 9/1983 | Redfern | |
| 4,560,381 A | 12/1985 | Southwell | |
| 4,581,772 A | 4/1986 | Smith | |
| 4,585,447 A | 4/1986 | Karami | |
| 4,610,680 A | 9/1986 | LaFleur | |
| 4,610,682 A | 9/1986 | Kopp | |
| 4,615,695 A | 10/1986 | Cooper | |
| 4,619,649 A | 10/1986 | Roberts | |
| 4,650,483 A | 3/1987 | Joffe | |
| 4,662,875 A | 5/1987 | Hirotsu et al. | |
| 4,663,220 A | 5/1987 | Wisneski et al. | |
| 4,699,622 A | 10/1987 | Toussant et al. | |
| 4,701,170 A | 10/1987 | Wilson et al. | |
| 4,701,176 A | 10/1987 | Wilson et al. | |
| 4,704,116 A | 11/1987 | Enloe | |
| 4,726,807 A | 2/1988 | Young et al. | |
| 4,743,239 A | 5/1988 | Cole | |
| 4,756,709 A | 7/1988 | Stevens | |
| 4,761,318 A | 8/1988 | Ott et al. | |
| 4,770,656 A | 9/1988 | Proxmire et al. | |
| 4,771,483 A | 9/1988 | Hooreman et al. | |
| 4,834,742 A | 5/1989 | Wilson et al. | |
| 4,850,988 A | 7/1989 | Aledo et al. | |
| 4,850,992 A | 7/1989 | Amaral et al. | |
| 4,894,060 A | 1/1990 | Nestegard | |
| 4,895,569 A | 1/1990 | Wilson et al. | |
| 4,936,840 A | 6/1990 | Proxmire | |
| 4,938,757 A | 7/1990 | Van Gompel | |
| 4,940,464 A | 7/1990 | Van Gompel et al. | |
| 4,963,140 A | 10/1990 | Robertson et al. | |
| 5,019,073 A | 5/1991 | Roessler et al. | |
| 5,032,122 A | 7/1991 | Noel et al. | |
| 5,046,272 A | 9/1991 | Vogt et al. | |
| 5,062,839 A | 11/1991 | Anderson | |
| 5,087,253 A | 2/1992 | Cooper | |
| 5,104,116 A | 4/1992 | Pohjola | |
| 5,176,670 A | 1/1993 | Roessler et al. | |
| 5,224,405 A | 7/1993 | Pohjola | |
| 5,226,992 A | 7/1993 | Mormon | |
| 5,242,436 A | 9/1993 | Weil et al. | |
| 5,256,231 A | 10/1993 | Gorman et al. | |
| 5,269,776 A | 12/1993 | Lancaster et al. | |
| 5,315,716 A | 5/1994 | Baum | |
| 5,326,612 A | 7/1994 | Goulait | |
| 5,342,341 A | 8/1994 | Igaue et al. | |
| 5,370,634 A | 12/1994 | Ando et al. | |
| 5,383,872 A | 1/1995 | Roessler et al. | |
| 5,399,219 A | 3/1995 | Roessler et al. | |
| 5,401,275 A | 3/1995 | Flug et al. | |
| 5,413,654 A | 5/1995 | Igaue | |
| 5,476,702 A | 12/1995 | Datta et al. | |
| 5,496,298 A | 3/1996 | Kuepper et al. | |
| 5,527,302 A | 6/1996 | Endres et al. | |
| 5,531,731 A | 7/1996 | Brusky | |
| 5,531,732 A | 7/1996 | Wood | |
| 5,546,608 A | 8/1996 | Russano | |
| 5,549,591 A | 8/1996 | Landvogt | |
| 5,554,239 A | 9/1996 | Datta et al. | |
| 5,591,155 A | 1/1997 | Nishikawa | |
| 5,595,567 A | 1/1997 | King et al. | |
| 5,603,708 A | 2/1997 | Seth | |
| 5,606,781 A | 3/1997 | Provost et al. | |
| 5,616,394 A | 4/1997 | Gorman et al. | |
| 5,620,432 A | 4/1997 | Goulait et al. | |
| 5,624,429 A | 4/1997 | Long et al. | |
| H1674 H | 8/1997 | Ames | |
| 5,655,843 A | 8/1997 | Conrad et al. | |
| 5,656,111 A | 8/1997 | Dilnik et al. | |
| 5,669,897 A | 9/1997 | Lavan | |
| 5,685,973 A | 11/1997 | Zones et al. | |
| 5,722,969 A | 3/1998 | Ito et al. | |
| 5,749,866 A | 5/1998 | Roe et al. | |
| 5,759,181 A | 6/1998 | Sayama et al. | |
| 5,766,389 A | 6/1998 | Brandon et al. | |
| 5,782,819 A | 7/1998 | Tanzer et al. | |
| 5,785,699 A | 7/1998 | Schmitz | |
| 5,795,350 A | 8/1998 | Schmitz | |
| 5,830,206 A | 11/1998 | Larsson | |
| 5,843,068 A | 12/1998 | Allen et al. | |
| 5,846,262 A | 12/1998 | Sayama et al. | |
| 5,851,205 A | 12/1998 | Hisada et al. | |
| 5,853,405 A | 12/1998 | Suprise | |
| 5,855,574 A | 1/1999 | Kling et al. | |
| 5,876,394 A | 3/1999 | Rosch et al. | |
| 5,879,500 A | 3/1999 | Herrin et al. | |
| 5,891,122 A | 4/1999 | Coates | |
| 5,897,545 A | 4/1999 | Kline et al. | |
| 5,897,546 A | 4/1999 | Kido et al. | |
| 5,899,895 A | 5/1999 | Robles et al. | |
| 5,906,008 A | 5/1999 | Heki et al. | |
| 5,911,713 A | 6/1999 | Yamada et al. | |
| 5,926,926 A | 7/1999 | Kato | |
| 5,967,665 A | 10/1999 | MacDonald et al. | |
| 5,997,521 A | 12/1999 | Robles et al. | |
| 6,022,430 A | 2/2000 | Blenke et al. | |
| 6,030,373 A | 2/2000 | VanGompel et al. | |
| 6,063,466 A | 5/2000 | Tuschy et al. | |
| 6,086,571 A | 7/2000 | Guevara et al. | |
| 6,099,516 A | 8/2000 | Pozniak et al. | |
| 6,113,717 A | 9/2000 | Vogt et al. | |
| 6,210,388 B1 | 4/2001 | Widland et al. | |
| 6,213,991 B1 | 4/2001 | Kling et al. | |
| 6,406,467 B1 | 6/2002 | Dilnik et al. | |
| 6,406,468 B1 | 6/2002 | Dilnik et al. | |
| 6,428,526 B1 | 8/2002 | Heindel et al. | |
| 6,454,751 B1 * | 9/2002 | Olson | 604/389 |
| 6,627,289 B1 | 9/2003 | Dilnik et al. | |
| 6,645,190 B1 | 11/2003 | Olson et al. | |
| 6,761,711 B1 | 7/2004 | Fletcher et al. | |
| 6,849,067 B2 | 2/2005 | Fletcher et al. | |
| 6,905,488 B2 | 6/2005 | Olson | |
| 6,994,698 B2 | 2/2006 | Leak et al. | |
| 7,156,833 B2 | 1/2007 | Couture-Dorschner et al. | |
| 2003/0100879 A1 | 5/2003 | Kline et al. | |

FOREIGN PATENT DOCUMENTS

| | | |
|---|---|---|
| EP | 0321232 B1 | 5/1993 |
| EP | 0476992 B1 | 7/1995 |
| EP | 0520087 A1 | 3/1996 |
| EP | 0433951 B1 | 8/1996 |
| EP | 0696911 B1 | 1/1997 |
| EP | 0570980 B1 | 7/1997 |
| EP | 0757550 B1 | 9/1998 |
| EP | 0878180 A2 | 3/1999 |
| EP | 0641552 B1 | 12/1999 |
| EP | 0756855 A1 | 2/2000 |
| EP | 0719534 B1 | 4/2000 |
| GB | 1520740 | 12/1975 |
| GB | 2267024 A | 11/1993 |
| GB | 2303045 A | 12/1997 |
| GB | 2315402 A | 4/1998 |
| JP | 5-84322 U | 11/1993 |
| JP | 6-30962 A | 2/1994 |
| JP | 6285113 A | 10/1994 |
| JP | 7116191 A | 5/1995 |
| JP | 9066071 A | 3/1997 |
| JP | 9187477 A | 7/1997 |
| WO | WO 93/17648 A1 | 9/1993 |
| WO | WO 95/02383 A1 | 1/1995 |
| WO | WO 95/18589 A1 | 7/1995 |
| WO | WO 95/27460 A1 | 10/1995 |
| WO | WO 95/27461 A1 | 10/1995 |
| WO | WO 95/27462 A1 | 10/1995 |
| WO | WO 95/27463 A1 | 10/1995 |
| WO | WO 95/29657 A1 | 11/1995 |
| WO | WO 96/19960 A1 | 7/1996 |
| WO | WO 96/41604 A1 | 12/1996 |
| WO | WO 97/04729 A1 | 3/1997 |
| WO | WO 97/23180 A1 | 7/1997 |
| WO | WO 97/36566 A1 | 10/1997 |

| | | |
|---|---|---|
| WO | WO 97/46197 | 12/1997 |
| WO | WO 97/46197 A1 | 12/1997 |
| WO | WO 97/48359 A1 | 12/1997 |
| WO | WO 98/18421 A1 | 5/1998 |
| WO | WO 98/18422 A1 | 5/1998 |
| WO | WO 99/53881 A1 | 10/1999 |
| WO | WO 99/65441 A1 | 12/1999 |

OTHER PUBLICATIONS

Written Opinion of the International Searching Authority of PCT/US2010/022410 dated Mar. 23, 2010.

* cited by examiner

ABSORBENT ARTICLE WITH INTERMITTENT SIDE SEAMS

FIELD OF THE INVENTION

The present invention relates generally to disposable absorbent garments such as disposable diapers, and more specifically to disposable diapers having side seams.

BACKGROUND OF THE INVENTION

Infants and other incontinent individuals wear disposable absorbent articles such as diapers to absorb and contain body exudates discharged from the body, particularly urine. Absorbent articles function to contain the discharged materials in isolation from the body of the wearer on one side, and from the wearers garments and/or bedding on the other. Absorbent articles are well known in the art and are typically constructed from a combination of liquid and vapor pervious and impervious materials which respectively allow the passage of liquid into the diaper and prevent its exit therefrom.

One type of absorbent article, known as a "training pant", is permanently or releasably seamed together to provide a pant-like product. In the case of releasable seams, the training pant can function so as to be applied either as a diaper or a pant. This is particularly useful for active children who are still in the training stages, since the releasable seams allow the product to be easily checked without having to pull the product downwards. Although not a complex maneuver, the separation of the releasable side seams still takes some effort, since a finger-lift portion must first be grasped before the side seams can be peeled away from one another. Also, when reattaching the side seams, the user must take care that the fastening components that make up the side seams are properly adhered to one another. Otherwise, the training pant may become undone while in use.

Accordingly, there is a need for an absorbent article having releasable side seams that are easily broken so that the interior of the article may be checked, and then easily reattached to continue use.

SUMMARY OF THE INVENTION

An absorbent article according to an exemplary embodiment of the present invention has an inside surface that faces a wearer's body when the absorbent article is worn, and an outside surface opposite the inside surface, and comprises: a liquid pervious topsheet; a liquid impervious backsheet; a front waist portion comprising a first side front panel and a second side front panel; a back waist portion comprising a first side back panel and a second side back panel; a crotch portion longitudinally extending between the front waist portion and the back waist portion; an absorbent assembly disposed between the topsheet and the backsheet; and a first fastening component disposed at the first side front panel and a second fastening component disposed at the second side front panel for respective attachment to the first side back panel and the second side back panel to fasten the absorbent article around the waist of the wearer, the first and second front fastening components each having at least one active fastening portion and at least one non-active fastening portion.

In at least one embodiment, the first and second front fastening components comprise hook elements.

In at least one embodiment, the at least one active fastening portion is formed by the hook elements.

In at least one embodiment, the at least one non-active fastening portion is formed by altered hook elements that are not capable of attaching to a corresponding one of the first and second side back panels.

In at least one embodiment, the at least one non-active fastening portion does not comprise the hook elements.

In at least one embodiment, the at least one non-active fastening portion comprises a fastening component outer layer that covers a portion of the hook elements to prevent the portion of hook elements from attaching to a corresponding one of the first and second side back panels.

In at least one embodiment, the first and second fastening components are disposed on the inside surface of the absorbent article.

In at least one embodiment, the first and second fastening components are disposed on the outside surface of the absorbent article.

In at least one embodiment, the first and second fastening components are directly attachable to the first side back panel and a second side back panel.

In at least one embodiment, the first and second fastening components make up a loopless fastening system In at least one embodiment, the topsheet is made of a nonwoven material.

In at least one embodiment, the backsheet is made up of an inner film layer and an outer nonwoven layer.

In at least one embodiment, the outer nonwoven layer of the backsheet extends laterally beyond the topsheet and the absorbent assembly to form the first and second side front panels and the first and second side back panels.

In at least one embodiment, the first side front panel, the second side front panel, the first side back panel and the second side back panel are each formed separately from the backsheet and the topsheet.

In at least one embodiment, the absorbent assembly comprises an acquisition/distribution layer and an absorbent core disposed below the acquisition/distribution layer.

Other features and advantages of the present invention will become readily apparent from the following detailed description, the accompanying drawings and the appended claims.

BRIEF DESCRIPTION OF THE DRAWINGS

The above and related objects, features and advantages of the present invention will be more fully understood by reference to the following, detailed description of the preferred, albeit illustrative, embodiment of the present invention when taken in conjunction with the accompanying figures, wherein.

DESCRIPTION OF THE PREFERRED EMBODIMENTS

As used herein, the term "absorbent article" refers to devices which absorb and contain body exudates, and more specifically, refers to devices which are placed against or in proximity to the body of the wearer to absorb and contain the various exudates discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

Figure 1:
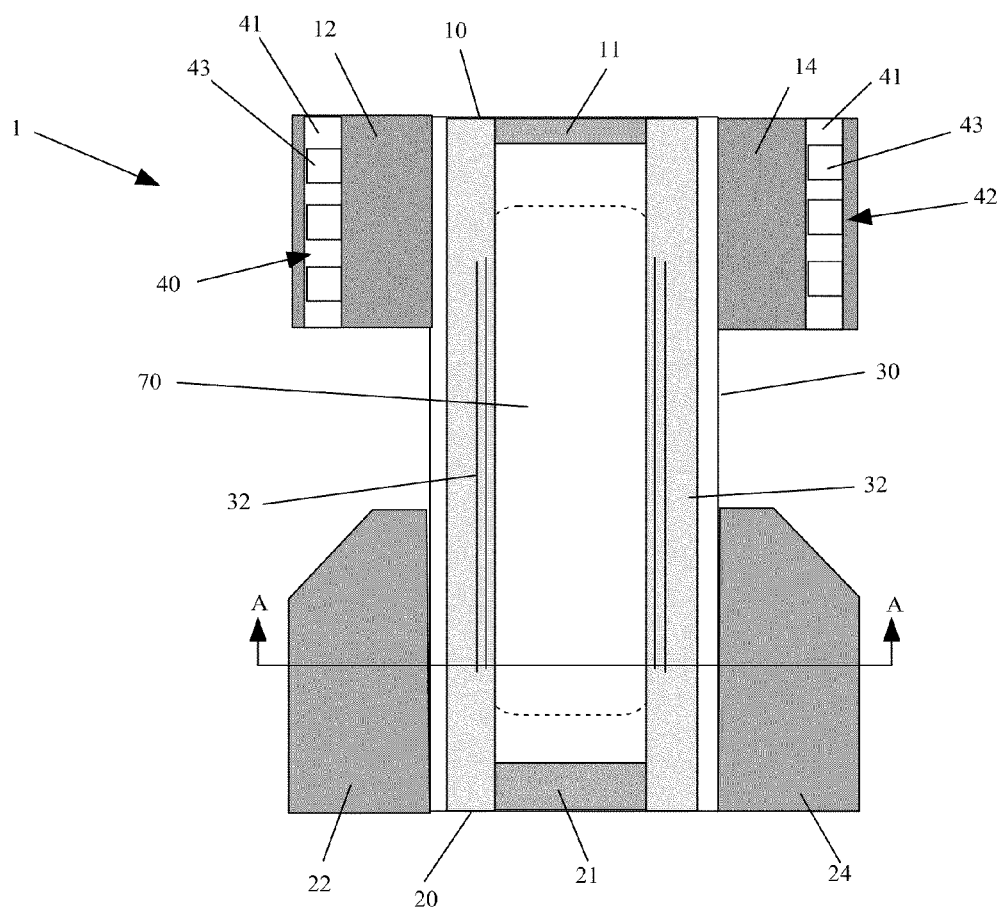
FIG. 1 is a plan view of the inner surface of an absorbent article according to an exemplary embodiment of the present invention.
Figure 2:
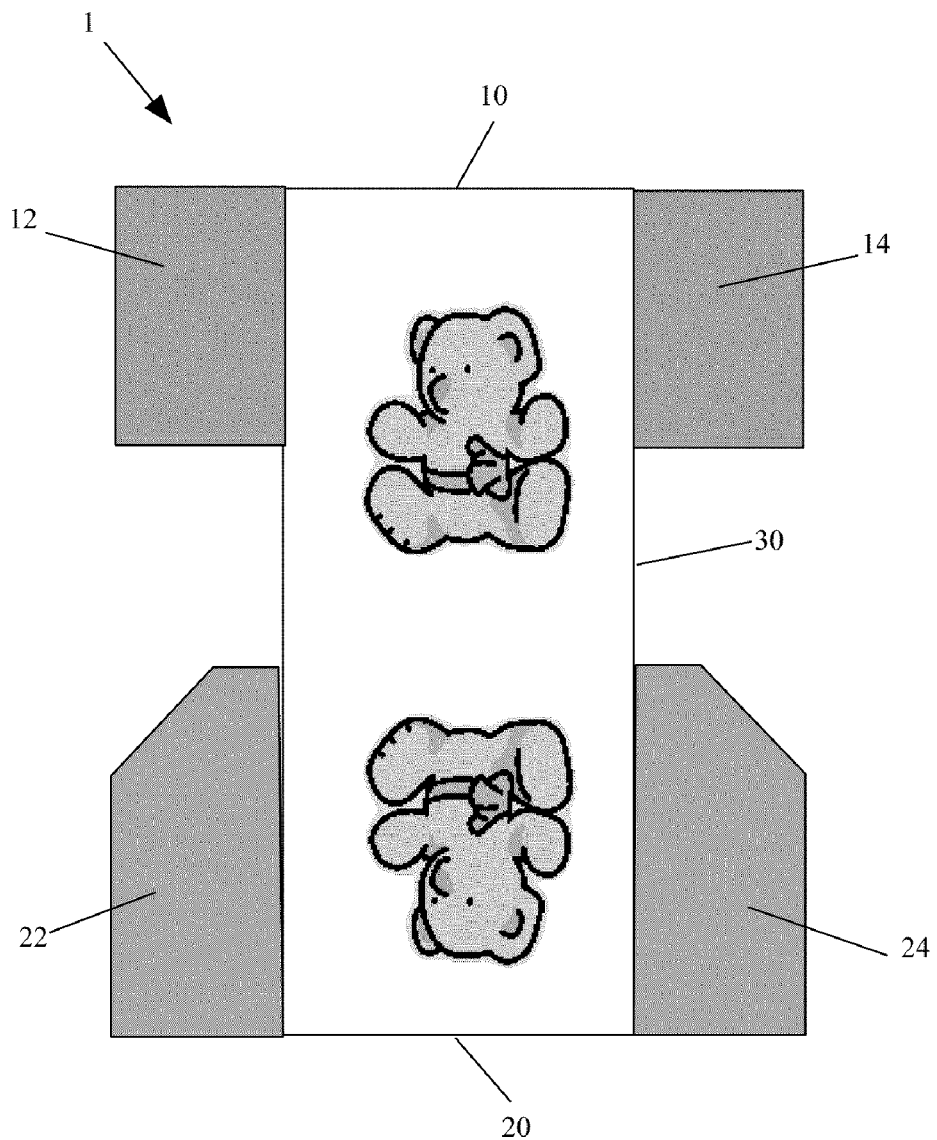
FIG. 2 is a plan view of the outer surface of an absorbent article according to an exemplary embodiment of the present invention.

FIGS. 1 and 2 are plan views of an absorbent article, generally designated by reference number 1, according to an exemplary embodiment of the present invention. In FIG. 1, the inside surface of the absorbent article 1 is facing upwards, and in the FIG. 2, the outside surface of the absorbent article 1 is facing upwards. The absorbent article 1 includes a front waist portion 10, a back waist portion 20, and a crotch portion 30 longitudinally extending between the front and back waist portions 10, 20. The front waist portion 10 includes a first side front panel 12 and second side front panel 14, and the back waist portion 20 includes a first side back panel 22 and a second side back panel 24. As explained in further detail below, the first side front panel 12 may be attached to the first side back panel 22 and the second side front panel 14 may be attached to the second side back panel 24 to form a training-pant type absorbent article to be pulled up around a wearer's waist.

Figure 3:
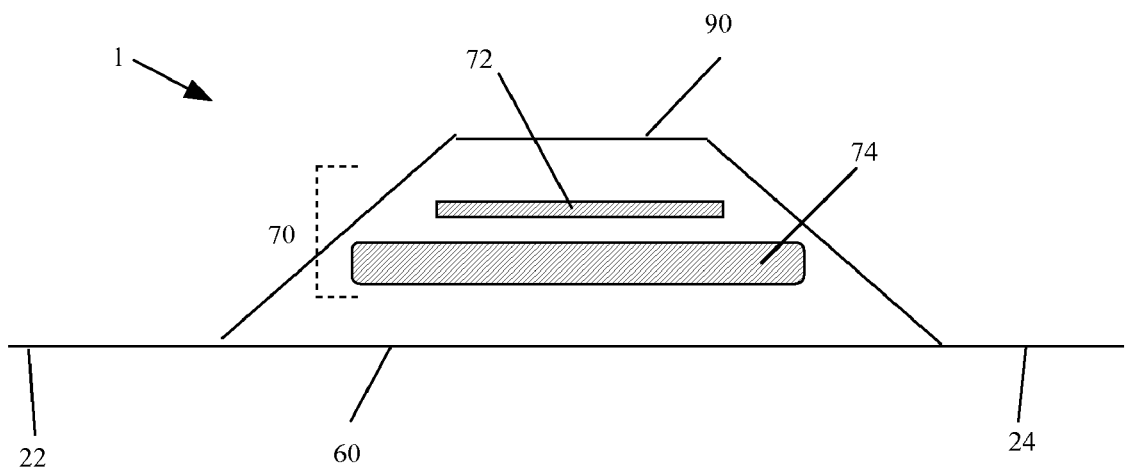
FIG. 3 is a cross-sectional view taken along the line A-A in FIG. 1.

FIG. 3 is a cross-sectional view of the absorbent article 1 taken along the line A-A of FIG. 1. As shown in FIG. 3, the absorbent article is a layered structure including a backsheet 60 and a topsheet 90. An absorbent assembly 70 is disposed between the backsheet 60 and topsheet 90. The absorbent assembly 70 includes an acquisition/distribution layer 72 and an absorbent member 74. In an exemplary embodiment, portions of the backsheet 60 extends beyond the other layers of the absorbent article 1 to form the first and second side front panels 12, 14 and the first and second side back panels 22, 24. However, it should be appreciated that, in other exemplary embodiments of the present invention, the first and second side front panels 12, 14 and first and second side back panels 22, 24 may be formed by extending portions of the topsheet 90, extending portions of both the backsheet 60 and topsheet 90, or by layering other materials with either one or both of the backsheet 60 and topsheet 90. In still other exemplary embodiments, the first and second side front panels 12, 14 and first and second side back panels 22, 24 may be formed separately from the backsheet 60 and topsheet 90. The first and second side front panels 12, 14 and the first and second side back panels 22, 24 may be made breathable, non-breathable, elastic, non-elastic, liquid pervious, liquid non-pervious, or include any other desired characteristic depending on the particular materials and construction used to form the side panels.

As shown in FIG. 1, the front waist portion 10 may include a front waist elastic 11 and the back waist portion 20 may include a back waist elastic 21. The front and back waist elastics 11, 21 provide elasticity to the waist of the absorbent article 1, so that the absorbent article 1 may have a snug fit with the wearer. As is known in the art, the front and back elastics 11, 21 may be made up of one or more elongated elastic elements extending transversely across the front and back waist portion 10, 20. In other exemplary embodiments of the present invention, only the front or back waist portions 10, 20 may include elasticized portions. Also, crotch elastics 32 may longitudinally extend through the crotch portion 30 to provide a snug fit in the crotch region of the absorbent article.

Figure 4:
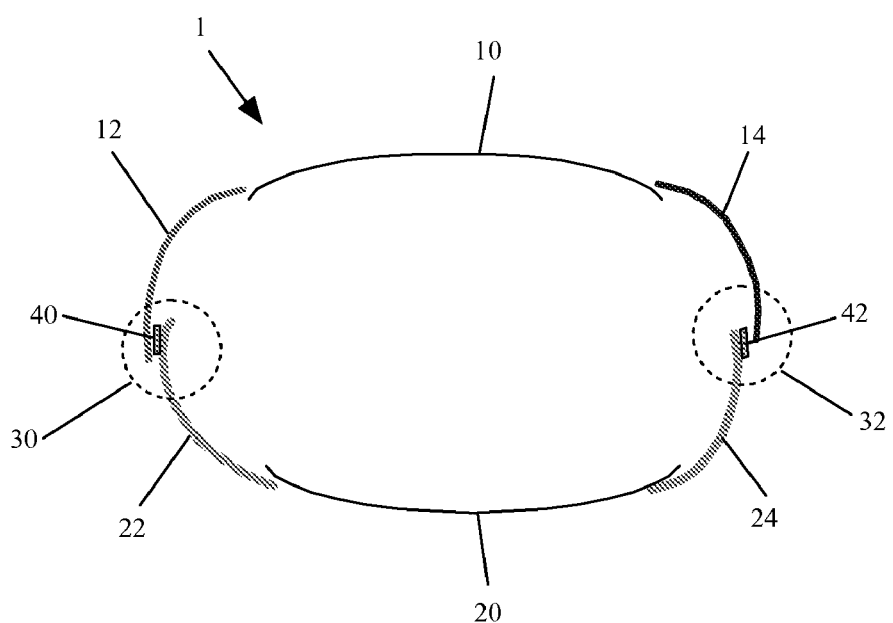
FIG. 4 is a simplified top view of an absorbent article in the fastened configuration according to an exemplary embodiment of the present invention.

In the an exemplary embodiment of the present invention, a first fastening component 40 is disposed on the inside surface of the first side front panel 12 and a second fastening component 42 is disposed on the inside surface of the second side front panel 14. As shown in FIG. 4, which is a simplified top view of the absorbent article 1 in the fastened configuration, the first and second fastening components 40, 42 may be used to fasten the first and second side front panels 12, 14 to the first and second side back panels 22, 24. In this configuration, the absorbent article 1 may be pulled up around the waist of a wearer so as to function as a training-pant. In this regard, the first and second fastening components 40, 42 form first and second side seams 30, 32 in the absorbent article 1 when in the fastened configuration.

In the present exemplary embodiment of the invention, the first and second fastening components 40, 42 form parts of a "loopless" fastening system. That is, the first and second fastening components 40, 42 include Velcro®-like hooks that are attachable to an outer nonwoven surface of the first and second side back panels 22, 24, respectively. Thus, the hooks of the first and second fastening components 40, 42 do not require special landing zones. Instead, the entire outer surface of the absorbent article 1 may function as a landing zone for the hooks so as to provide an increased degree of flexibility in the fitting of the absorbent article 1 to a wearer. Such a loopless fastener system is described in U.S. Patent Application Publication No. US 2003/0220626 A1, filed on May 7, 2003, now abandoned, and in U.S. Patent Application Publication No. 2008-0132867, filed Nov. 30, 2006, the contents of which are incorporated herein by reference.

As shown in FIG. 1, each of the first and second fastening components 40, 42 include one or more active fastening portions 41 and one or more non-active fastening portions 43. As discussed in greater detail below, the non-active fastening portions 43 are not capable of attachment to the outer surface of the absorbent article 1, so that the side seams 30, 32 are effectively made intermittent. The intermittent side seams 30, 32 allow the user to protrude his finger into the non-active portions 43 of one of the side seams 30, 32 and pull the first and second fastening components 40, 42 from the first and second side back panels 22, 24 to break the side seams 30, 32. Each active fastening portion 41 may have a longitudinal length within the range of approximately 10 to 50 mm, and each non-active fastening portion 43 may have a longitudinal length of approximately 5 to 25 mm. In a preferred embodiment of the present invention, the intermittent side seams 30, 32 include approximately 14 mm in length of active fastening portions 41 and approximately 6 mm in length of non-active fastening portions in repeating pattern. The number of non-active fastening portions 43 may be approximately 4. In a preferred exemplary embodiment, the area of the active fastening portions 41 occupies less than approximately 70% of the total area of the side seams 30, 32 so as to provide proper balance between providing a secure side seam and ease in separation of the side seam.

Figure 5A:
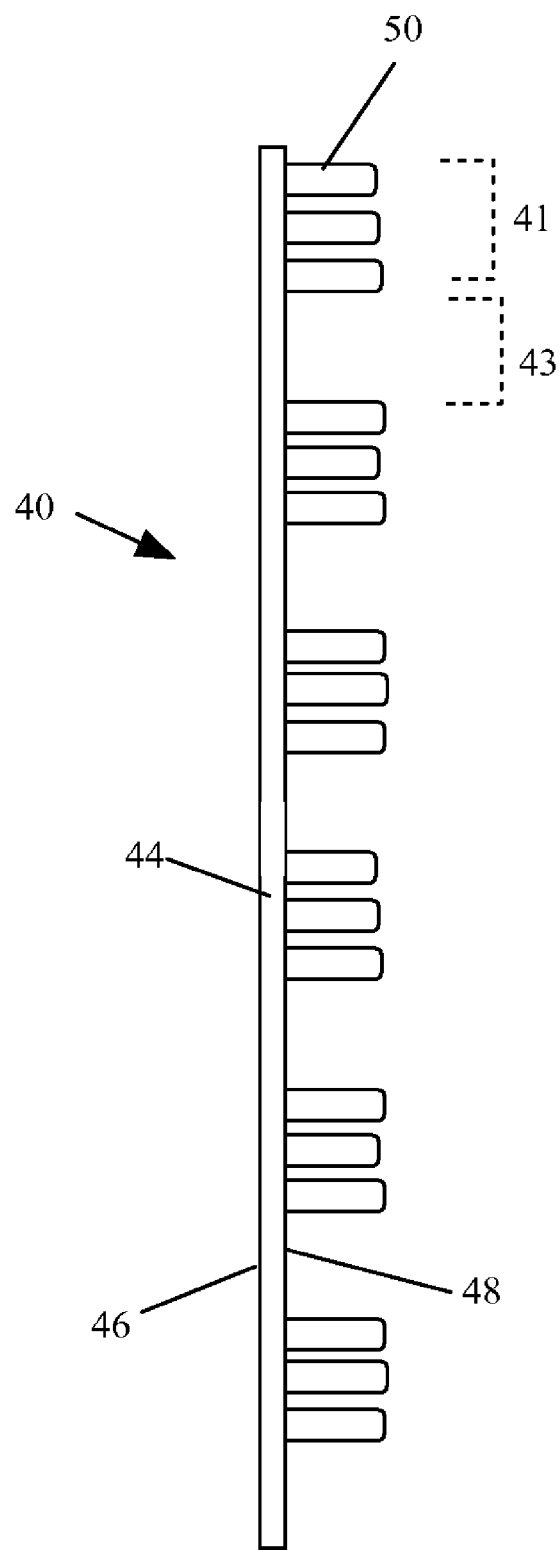
FIGS. 5A-5C are side views of a fastening component according to various exemplary embodiments of the present invention.
Figure 5B:
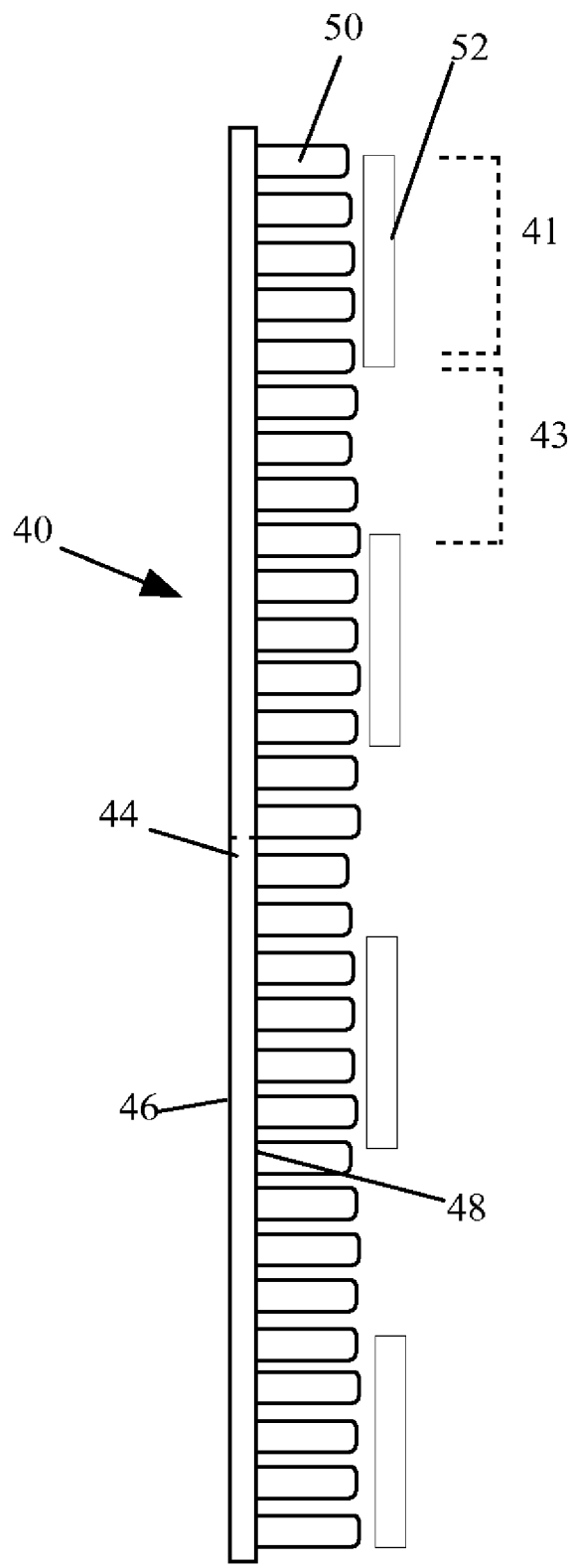
Figure 5C:
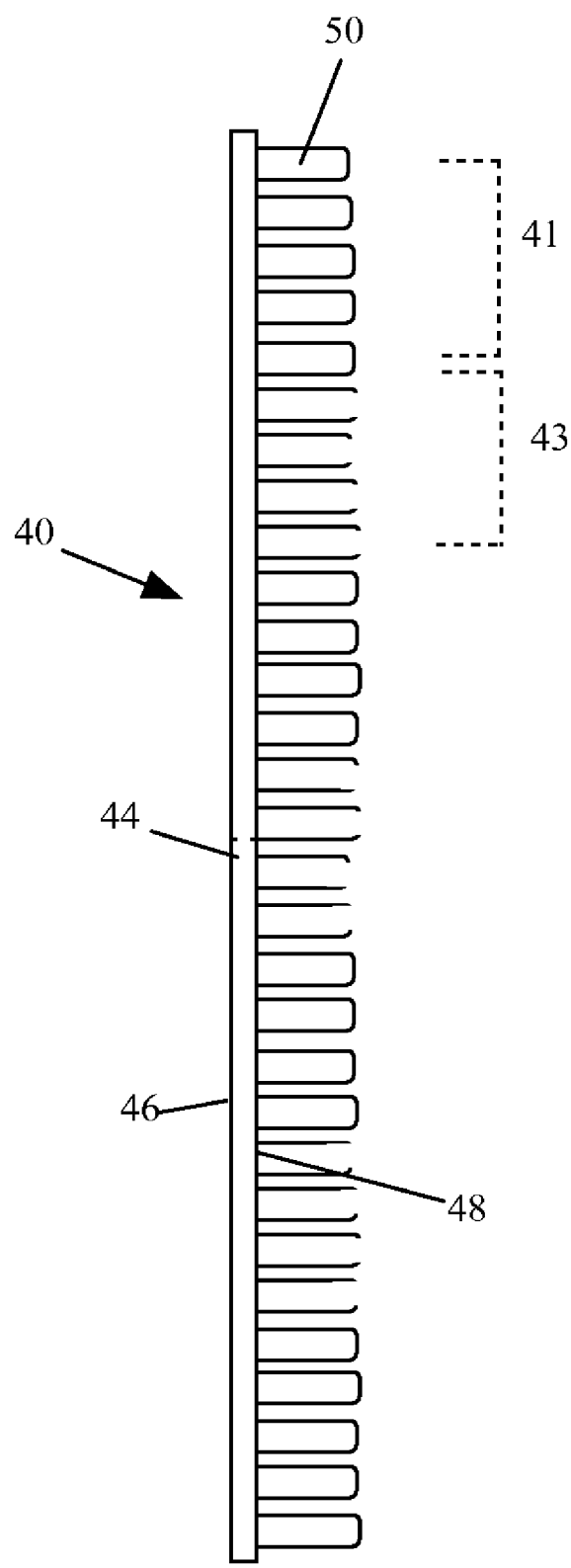

The structure of the first fastening component 40 will now be described. A description of the second fastening component 42 is omitted here, as it should be understood that the second fastening component 42 may have the same structure as that of the first fastening component 40. FIGS. 5A-4C are side views of the first fastening component 40. The first fastening component 40 includes a base layer 44 having a back surface 46 and a front surface 48. The base layer 44 may be, for example, a nonwoven material layer or a polymeric material layer. The back surface 46 may be attached to the inner surface of the first side front panel 12 (or the inner surface of the second side front panel 14 in the case of the second fastening component 42) by, for example, adhesive, ultrasonic or thermal sealing. The front surface 48 of the first fastening component 40 includes the one or more active fastening portions 41 and the one or more non-active fastening portions 43. In this regard, as shown in FIG. 5A, hook elements 50 may protrude from the front surface 48 of the first fastening component 40 within the active fastening portions 41, while the front surface 48 may be left bare (i.e., without hook elements) in the non-active fastening portions 43. In another exemplary embodiment, as shown in FIG. 5B, the hook elements 50 may protrude from and cover the entire front surface 48 of the first fastening component 40, and one or more blocking layers 52 may be disposed intermittently over the hook elements 50 to form the non-active fastening portions 43. The blocking layers 52 may be made of, for example, nonwoven material or polymeric film material, and may be attached to the hook elements 50 by, for example, adhesive. In another exemplary embodiment, as shown in FIG. 5C, the hook elements 50 may protrude from and cover the entire front surface 48 of the first fastening component 40, with the hook elements 50 being altered within the non-active fastening portions 43 so as to be made incapable of attaching to the first side back panel 22. For example, the hook elements 50 within the non-active fastening portions 43 may be damaged in that the hooks may be opened up or otherwise rendered inoperable.

Topsheet 90 may be made of any suitable relatively liquid-pervious material currently known in the art or later discovered that permits passage of a liquid therethrough. Examples of suitable top sheet materials include nonwoven, spun-bonded or carded webs of polypropylene, polyethelene, nylon, polyester and blends of these materials, or perforated, apertured or reticulated films, and the like. Nonwoven materials are exemplary because such materials readily allow the passage of liquids to the underlying acquisition layer 72, and therethrough to absorbent core 74. The top sheet 90 is preferably formed of a single ply of nonwoven material that may be made of thermally bonded, spunbonded fibers, spunbond-meltblown-spunbond or fibers that have been hydroentangled, having a basis weight of, for example, 10-30 grams per square meter and having appropriate strength and softness for use as a topsheet in an application which will be in contact with human skin. Topsheet 90 may be treated with surfactant, rendering it hydrophilic to facilitate the passage of moisture through topsheet 90 and into the interior of absorbent assembly 70. The present invention is not intended to be limited to any particular material for top sheet 90 and other top sheet materials will be readily apparent to those skilled in the art.

Acquisition/distribution layer 72 may be a single layer or multiple layers made of synthetic or natural material, or a combination of both, or a single multilayer apertured film. Acquisition/distribution layer 72 serves to quickly collect and distribute discharged body fluid to absorbent core 74. Because such fluid is typically discharged in gushes, the area of absorbent core 74 proximate to the point of fluid discharge may be overwhelmed by its rate, resulting in a leak. Therefore, the acquisition/distribution layer 72 facilitates transport of the fluid from the point of discharge across its surface area to contact other parts of absorbent core 74 from which it can be more readily absorbed. The use of an acquisition/distribution layer is well known in the art. Accordingly, acquisition/distribution layer 74 of the absorbent article 1 may have any well known or as yet undiscovered construction. Alternatively, absorbent core 26 may have the construction disclosed in U.S. Pat. Nos. 6,068,620 and 6,646,180 to Chmielewski, both of which are hereby incorporated by reference.

Absorbent core 74 may be any absorbent material which is generally compressible, conformable to the shape of the wearer's body and will not impede normal movement by the wearer, and capable of absorbing and retaining liquids such as urine and certain other body exudates. The absorbent core 74 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles, such as, for example, wood pulp fluff. Examples of other suitable absorbent materials include creped cellulose wadding; meltblown polymers; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of absorbent core 74 may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs. In addition, each member need not be formed of a single unitary piece of material, but may be formed of a number of smaller strips or components joined together lengthwise or width-wise, as long as they are in fluid communication with one another.) The total absorbent capacity of absorbent core 74 should, however, be compatible with the design loading and the intended use of the absorbent article 1. Further, the size and absorbent capacity of the absorbent core 74 may be varied to accommodate wearers ranging from infants through adults.

Backsheet 60 may be made of an inner layer of film that is suitably pliable and liquid impervious and an outer layer of a liquid and/or vapor-pervious material. Typical materials for the backsheet 60 inner layer include films of polyethylene, polypropylene, polyester, nylon and polyvinyl chloride and blends of these materials. For example, the inner layer may be made of a polyethylene film having a thickness in the range of 0.5 to 2.0 mils. Other backsheet inner layer materials may be readily apparent to those skilled in the art. Backsheet inner layer preferably has sufficient liquid imperviousness to prevent any leakage of fluids. The required level of liquid imperviousness may vary between different locations on absorbent article 1. Accordingly, the backsheet inner layer may be made vapor pervious or multi layered, having varying degrees of liquid-imperviousness.

The outer layer of the backsheet 60 may be made of a liquid and/or vapor-pervious material which may be selected from the same group of materials from which the top sheet was selected. The inner layer of the backsheet 60 may have a basis weight of, for example, between 5-45 grams per square meter. Unlike topsheet 90, however, the material used for the outer layer of the backsheet 60 is preferably rendered hydrophobic by omitting the surfactant discussed above with respect to topsheet 90. The outer layer of the backsheet 60 may be manufactured by well known methods such as thermal bonding, chemical bonding, spun bonding and hydroentanglement, or by a combination of spun bonding and hydroentanglement.

Backsheet 60 preferably has the same or greater longitudinal dimension to that of absorbent assembly 70. Also, the lateral dimension of at least the inner layer of the backsheet 60 is preferably greater than that of the absorbent assembly 70. In this regard, as discussed above, the inner layer and the outer layer, or only the outer layer, of the backsheet 60 may extend beyond the absorbent assembly 70 to form that first and second side front panels 12, 14 and the first and second side back panels 22, 24.

Absorbent assembly 70 may be self contained, for example by adhering the perimeter of topsheet 90 to the inner layer of the backsheet 60, such as with ordinary adhesive, or by bonding, with heat or ultrasonically, the components to each other. In such a construction, acquisition/distribution layer 72 and absorbent core 74 are contained within a package formed by the inner layer of the backsheet 60 and the topsheet 90. Absorbent assembly 70 may then be adhered to outer layer of the backsheet 60. Alternatively, topsheet 90 may be adhered directly to the outer layer of the backsheet 60, so that the topsheet 90 secures the components of the absorbent assembly 70 between the backsheet 60 and the topsheet 90.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having an inside surface that faces a wearer's body when the absorbent article is worn, and an outside surface opposite the inside surface, the absorbent article comprising:
    a liquid pervious topsheet;
    a backsheet, at least a portion of the backsheet being liquid impervious;
    a front waist portion comprising a first side front panel and a second side front panel;
    a back waist portion comprising a first side back panel and a second side back panel;
    a crotch portion longitudinally extending between the front waist portion and the back waist portion;
    an absorbent assembly disposed between the topsheet and the backsheet; and
    a first fastening component disposed at the first side front panel and a second fastening component disposed at the second side front panel for respective attachment to the first side back panel and the second side back panel to fasten the absorbent article around the waist of the wearer, the first and second fastening components each having at least one active fastening portion and at least one non-active fastening portion, the first and second fastening components comprising hook elements, the at least one non-active fastening portion being formed by altered hook elements that are not capable of attaching to a corresponding one of the first and second side back panels.

2. The absorbent article of claim 1, wherein the at least one active fastening portion is formed by the hook elements.

3. The absorbent article of claim 1, wherein the at least one non-active fastening portion comprises a fastening component outer layer that covers a portion of the hook elements to prevent the portion of hook elements from attaching to a corresponding one of the first and second side back panels.

4. The absorbent article of claim 1, wherein the first and second fastening components are disposed on the inside surface of the absorbent article.

5. The absorbent article of claim 1, wherein the first and second fastening components are disposed on the outside surface of the absorbent article.

6. The absorbent article of claim 1, wherein the first and second fastening components are directly attachable to the first side back panel and the second side back panel.

7. The absorbent article of claim 1, wherein the first and second fastening components make up a loopless fastening system.

8. The absorbent article of claim 1, wherein the topsheet is made of a nonwoven material.

9. The absorbent article of claim 1, wherein the backsheet is made up of an inner film layer and an outer nonwoven layer.

10. The absorbent article of claim 9, wherein the outer nonwoven layer of the backsheet extends laterally beyond the topsheet and the absorbent assembly to form the first and second side front panels and the first and second side back panels.

11. The absorbent article of claim 1, wherein the first side front panel, the second side front panel, the first side back panel and the second side back panel are formed separately from the backsheet and the topsheet.

12. The absorbent article of claim 1, wherein the absorbent assembly comprises an acquisition/distribution layer and an absorbent core disposed below the acquisition/distribution layer.

* * * * *